United States Patent [19]
Marshall

[11] Patent Number: 5,805,270
[45] Date of Patent: Sep. 8, 1998

[54] DEVICE AND METHOD FOR TESTING FIELD OF VISION

[76] Inventor: Forrest A. Marshall, 615 Academy Ave., Dublin, Ga. 31021

[21] Appl. No.: 648,581

[22] Filed: May 16, 1996

[51] Int. Cl.[6] .................................. A61B 3/02; A61B 3/00
[52] U.S. Cl. ............................................ 351/222; 351/246
[58] Field of Search ...................................... 351/224, 225, 351/223, 222, 245, 246, 200, 226

[56] References Cited

U.S. PATENT DOCUMENTS

| | | | |
|---|---|---|---|
| 4,169,664 | 10/1979 | Bailey, Jr. . | |
| 4,522,474 | 6/1985 | Slavin | 351/203 |
| 4,685,784 | 8/1987 | Kirchhuebel | 351/226 |
| 4,871,247 | 10/1989 | Haynes . | |
| 5,293,532 | 3/1994 | Marshall | 351/225 |
| 5,459,536 | 10/1995 | Shalon et al. | 351/226 |
| 5,461,436 | 10/1995 | Campbell | 351/242 |

*Primary Examiner*—Hung X. Dang
*Attorney, Agent, or Firm*—Dean W. Russell; Michael F. Labbee; Kilpatrick Stockton LLP

[57] ABSTRACT

An apparatus for performing assessments of field of vision that is portable, does not require the patient to adopt a particular posture or position relative to the testing device and may be operated so as to require minimal active responses from the patient is disclosed. The invention includes a patch, cover, or other device designed to occlude from ambient light and visually stimulate the subject eye. The interior of the patch facing the occluded eye includes an array of light sources, such as LEDs or LCD pixels, selective and sequential illumination of each source being controlled electrically by the practitioner, either manually or via a computer controller. The close proximity of the light sources to the eye being tested also minimizes anomalous results arising from poor visual acuity.

16 Claims, 3 Drawing Sheets

DEVICE AND METHOD FOR TESTING FIELD OF VISION

FIELD OF THE INVENTION

This invention relates to apparatus and techniques for testing field of vision.

BACKGROUND OF THE INVENTION

The determination of an individual's field of vision, i.e., the entire area visible to the immobile eye at a given moment, can provide valuable information to medical personnel in a variety of settings. In particular, an accurate assessment of field of vision can give insight into the status of the individual's optical pathway and cerebral function. An abnormal field of vision may be evidence of damage to the visual pathway resulting from trauma, intrusion (such as a tumor), or pressure (from a tumor or aneurysm). As can be seen in FIG. 1, for instance, damage to one of the optic nerves can result in loss of vision in one eye; damage at the point where the optic nerves from each eye cross over into the opposite lobe of the brain can result in loss of vision in outside halves of the field of vision in each eye; and so on. Thus, by determining the extent and severity of loss of field of vision, the practitioner can identify the approximate location and the extent of damage to the visual pathway.

A conventional apparatus for performing an assessment of a patient's field of vision is illustrated in U.S. Pat. No. 5,461,436 to Campbell. The patient's head is placed in a large partially spherical structure (typically four to six feet in diameter). The patient focuses on a central fixation light while beams of light (the "test signals") are briefly projected onto various points on the inner surface of the structure. The patient responds, either verbally or by depressing a switch, when he or she observes a test signal. While the conventional method of assessment is effective in accurately characterizing the scope of the patient's field of vision, it may be impractical in many situations where an assessment is desirable. For instance, it may be desirable to perform an assessment in a bedridden patient's hospital room; in the field during an emergency call; or at a doctor's office, where space might be at a premium.

Furthermore, the conventional means for performing an assessment may be inaccurate or even unusable with particular classes of patients. For example, a small child may be too young to understand that a test is being performed and may be unwilling to cooperate. Similarly, a patient who is disabled or injured may not be able to press a button or even respond verbally upon observing a test signal. Likewise, a person with poor vision may have difficulty in observing a test signal, not for lack of peripheral vision, but for lack of visual acuity. In other words, a patient with severe myopia may not be able to see test signals clearly, even at a distance of only four to six feet. As a result, the patient may fail to observe test signals that are otherwise within the patient's peripheral vision simply because he or she cannot adequately focus on the test signal. Corrective optics may be used resolve the patient's myopia, however, the correct prescription may not always be available, such as in field emergencies or in a patient's hospital room. Furthermore, other visual dysfunctions which cannot be corrected with optics, such as cataracts, can also interfere with test results.

SUMMARY OF THE INVENTION

The present invention provides an apparatus for performing assessments of field of vision that is portable and does not require the patient to adopt a particular posture or position relative to the testing device. The invention also allows field of vision to be measured while requiring minimal active responses from the patient. The invention includes a patch, cover, or other device designed to occlude from ambient light and visually stimulate the subject eye. The interior of the patch facing the occluded eye includes an array of light sources, such as LEDs or LCD pixels, selective and sequential illumination of each source being controlled electrically by the practitioner, either manually or via a computer controller.

To perform an assessment of a patient's field of vision, the device is secured to the patient's head with the patch over the subject eye. The practitioner illuminates a central one (or ones) of the light sources within the patch and asks the patient to fixate on the source. Other of the sources are then illuminated briefly and sequentially. In this manner, test signals are provided in a sequence that results in substantially all areas of a normal visual field being illuminated by at least one test signal over the course of the assessment. If the patient observes the test signal, he or she is instructed to respond verbally, by pressing a button or by signaling the practitioner in some fashion.

If the patient cannot respond verbally or manually, due to some incapacity, the practitioner can instruct the patient to look towards any observed test signals. The practitioner then observes the uncovered eye. Because both eyes tend to act in coordination, the uncovered eye likely will follow the movement of the covered eye. The practitioner, observing the movement of the uncovered eye, can conclude that the test signal was detected.

Because the device need only be large enough to occlude the subject eye, it is easily made portable. Also, the device can be held with a strap secured about the patient's head. Thus, the device may be used to perform assessments on patients who are supine or prone and unable to adopt the position required to participate in a conventional assessment. Testing equipment, such as a power supply control circuitry and a control panel may be incorporated into the patch itself or provided in a separate package, which also may be portable. Thus, the device may be used in many situations where use of the conventional apparatus for assessing field of vision would be impractical or impossible, such as hospital rooms and field emergencies.

Because the source of the test signals are very near to the subject eye, the image of the test signal, while appearing to the brain to be at infinity, is clearly visible. A patient's lack of visual acuity will have less of a tendency to affect the accuracy of the exam because the patient need not focus on a point approximately three to six feet away and would be less fatiguing to the patient. Thus, there is less likelihood that the patient's lack of visual acuity will cause him or her to fail to observe test signals, avoiding anomalous test results.

It is therefore an object of the present invention to provide a means for assessing a person's field of vision that is both portable and compact.

It is another object of the present invention to provide a means for assessing a person's field of vision where the test can be performed on persons who are at least partially incapacitated.

It is another object of the present invention to provide a means for assessing a person's field of vision that will provide accurate results even though the subject may have imperfect visual acuity.

Other objects, features, and advantages of the present invention will become apparent with reference to the remainder of the written portion and the drawings of this application.

DETAILED DESCRIPTION

Figure 1:
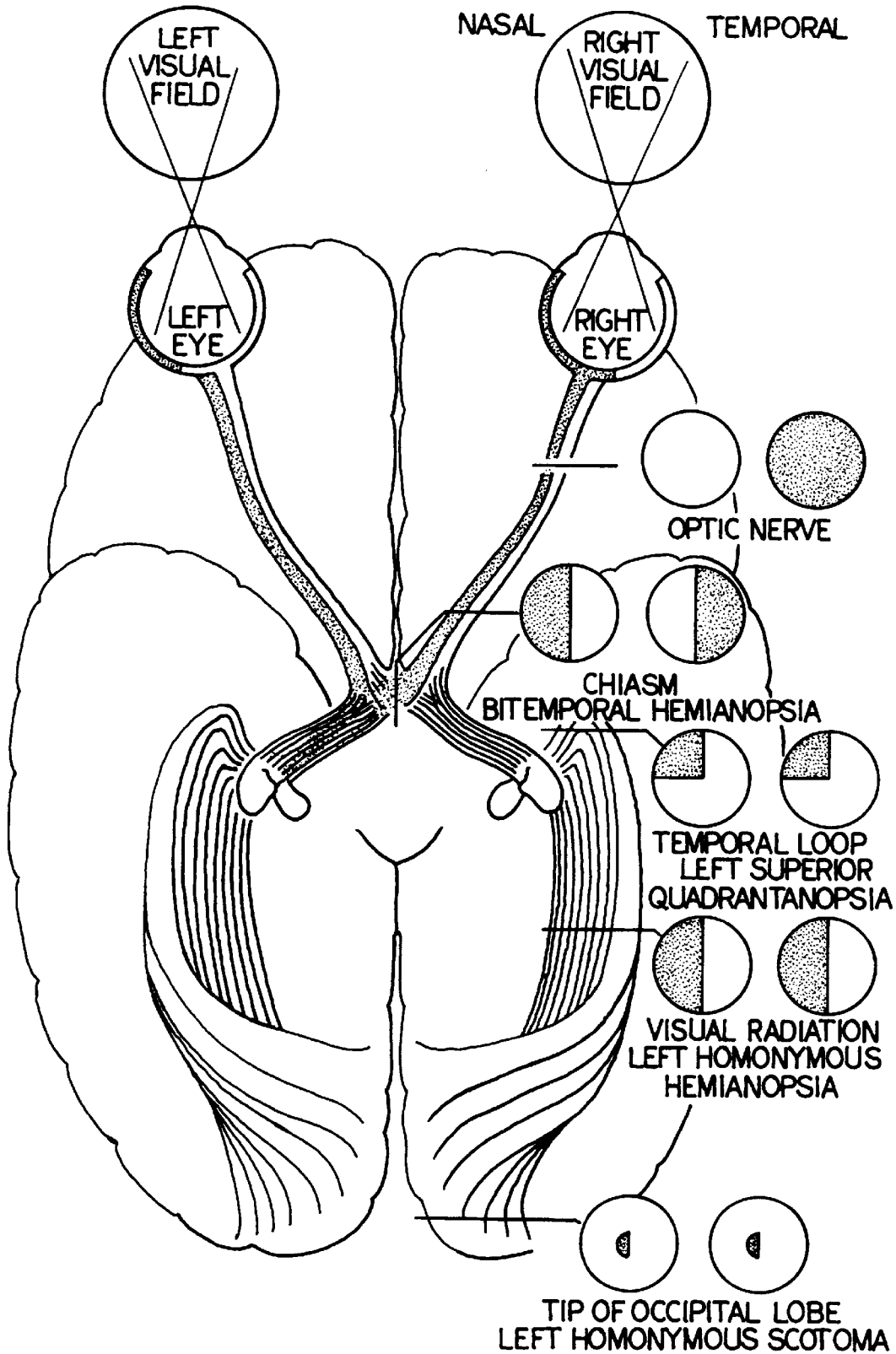
FIG. 1 is a diagram showing the effect of damage to the optical pathway on field of vision.
Figure 2:
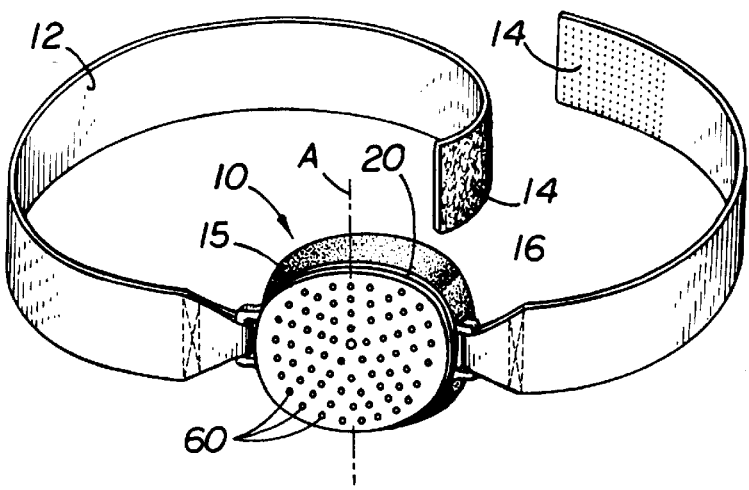
FIG. 2 is a perspective view of a first embodiment of the present invention.

FIG. 2 illustrates a first embodiment of device 10 of the present invention. Band 12 is attached to device 10 and includes hook and loop fasteners 14 or other suitable means for securing device 10 about the patient's head. Device 10 includes illumination unit 15 and eye piece 16. Eye piece 16 conforms to the patient's facial contours and creates a substantially light fast seal around the patient's eye. Because facial contours surrounding the eyes of most patients are approximately symmetrical, eye piece 16, if fitted to one of left and right eyes need merely be rotated 180° about axis A to adapt it for use with the other eye. Locking ring 20 is provided to secure the position of eye piece 16 once fitted to an eye. Alternatively, eye piece 16 may be designed for use with both eyes without rotation, for instance, having a bellows for adjusting to the facial contours surrounding both the left and right eyes of the patient.

Figure 4:
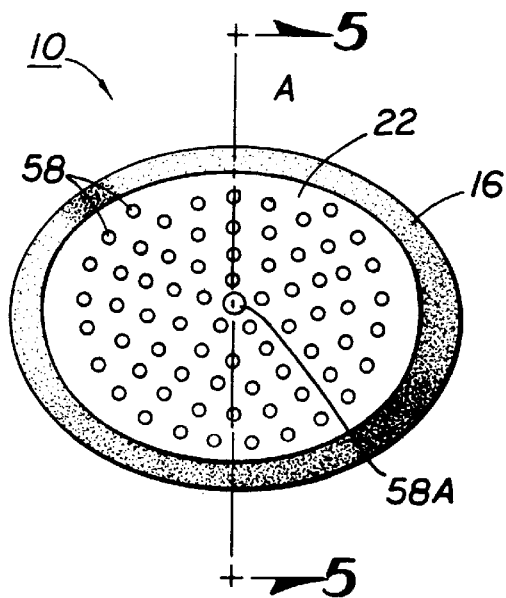
FIG. 4 is a rear view of an embodiment of the present invention employing an LED array.
Figure 5:
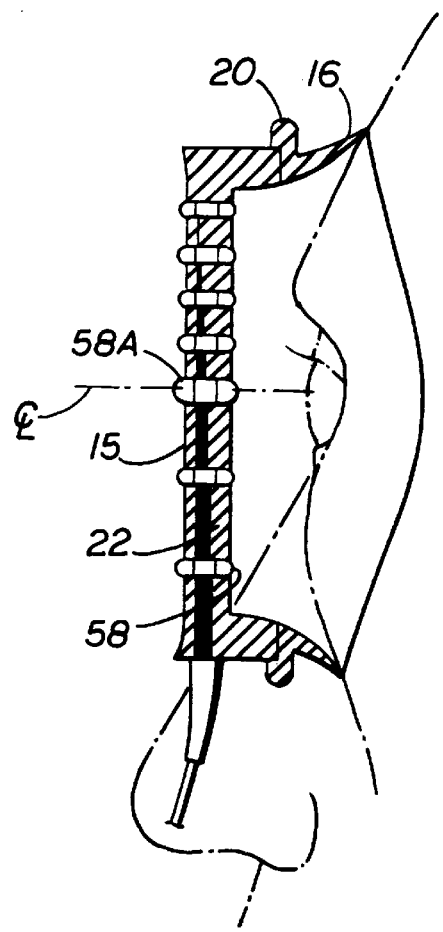
FIG. 5 is a cross sectional view of the embodiment of FIG. 4.

Referring to FIGS. 4 and 5, device 10 includes an array of light sources 58 mounted on unit 15. Because unit 15 is designed to occlude a patient's eye from ambient light, it includes an opaque wall or backing 22 behind sources 58. Light sources 58 may be LEDs, LCD pixels, fiber optics, incandescent or fluorescent light-emitting sources, or any other suitable means for providing light at frequencies in the visible spectrum. Light sources 58 are distributed within unit 15 so as to span the entire scope of a normal field of vision, i.e., when device 10 is placed over the subject eye, the distribution of light sources 58 extends to or beyond the limits of peripheral vision of a normal patient. A fixation source 58A is positioned so that it is directly in the center of the patient's field of vision when the patient is looking straight ahead.

Figure 6:
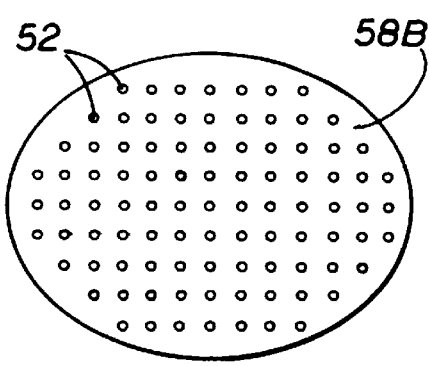
FIG. 6 is a rear view of an embodiment of the present invention employing an LCD array.
Figure 7:
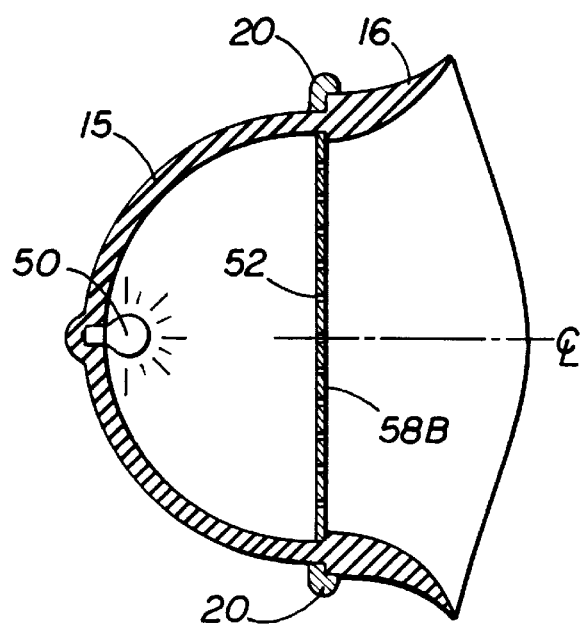
FIG. 7 is a cross sectional view of the embodiment of FIG. 7.

Regardless of the type of light source used, each source 58 may be independently illuminated. For instance, if LEDs are used, as shown in FIGS. 4 and 5, each LED may be connected to a separate switch and then to a power source. The switches are operated, either manually or by a control unit, to illuminate selectively LEDs in accordance with a testing sequence. If LCD pixels are used, as in FIGS. 6 and 7, a single illumination source 50 is provided which remains illuminated at all times during the operation of device 10. LCD array 52 is interposed between the illumination source 50 and the patient's eye. To "turn on" a pixel, a desired pixel 58B is rendered transparent, allowing light to pass through LCD array 52 at that point. Of course, arrays other than that shown in FIGS. 4–7 may be used in accordance with the present invention as long as they provide sufficient coverage to test the full range of field of vision.

Figure 2A:
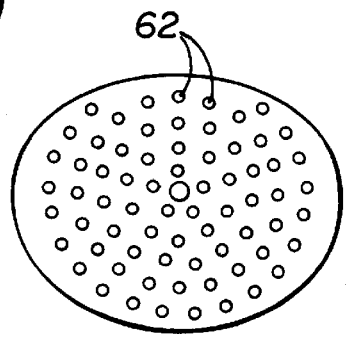
FIG. 2A is a front view of an alternate embodiment of the device of FIG. 2.

Device 10 may be self contained, as in FIG. 2, thus including a battery and control circuitry, which may contain an onboard memory for story preprogrammed control sequences. Device 10 may also contain either a series of external switches 60 or external lights 62 (FIG. 2A), corresponding to the internal light sources. Device 10 can be operated automatically, in response to voice commands or by depressing one or more of external switch 60 in a predetermined pattern to initiate a preprogrammed test sequence. Device 10 can also operate manually where the practitioner illuminates each interior light 58 source by pressing a corresponding external switches 60. Referring to FIG. 2A, sources 62 may be placed on the outer face of device 10 so as to correspond to sources 58 in a one-to-one relationship, providing the practitioner with visible confirmation of the particular source or sources 58 which are illuminated at any given time. Of course, any other suitable means for confirming which sources 58 are illuminated may be employed as alternatives to light sources 62. Depending on the type of light sources 58 selected and the functions to be performed by device 10, additional electric circuitry may be connected to the device 10 as necessary to serve as an interface with other electric or electronic components such as (but not limited to) a computer or provide means for the practitioner to monitor the status of each light source 58 during the examination or procedure.

Figure 3:
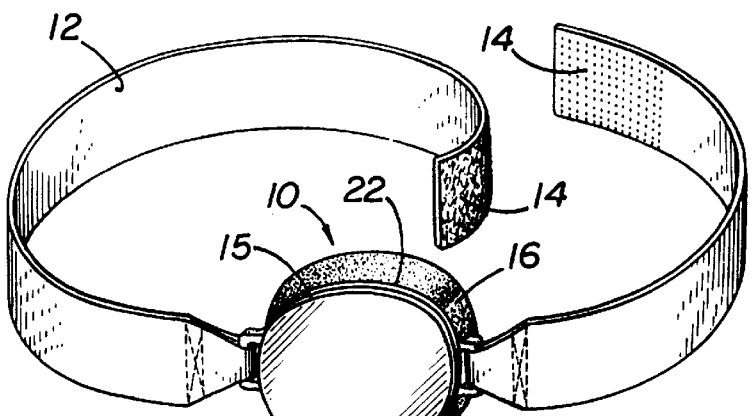
FIG. 3 is a perspective view of a second embodiment of the present invention.
Figure 3:
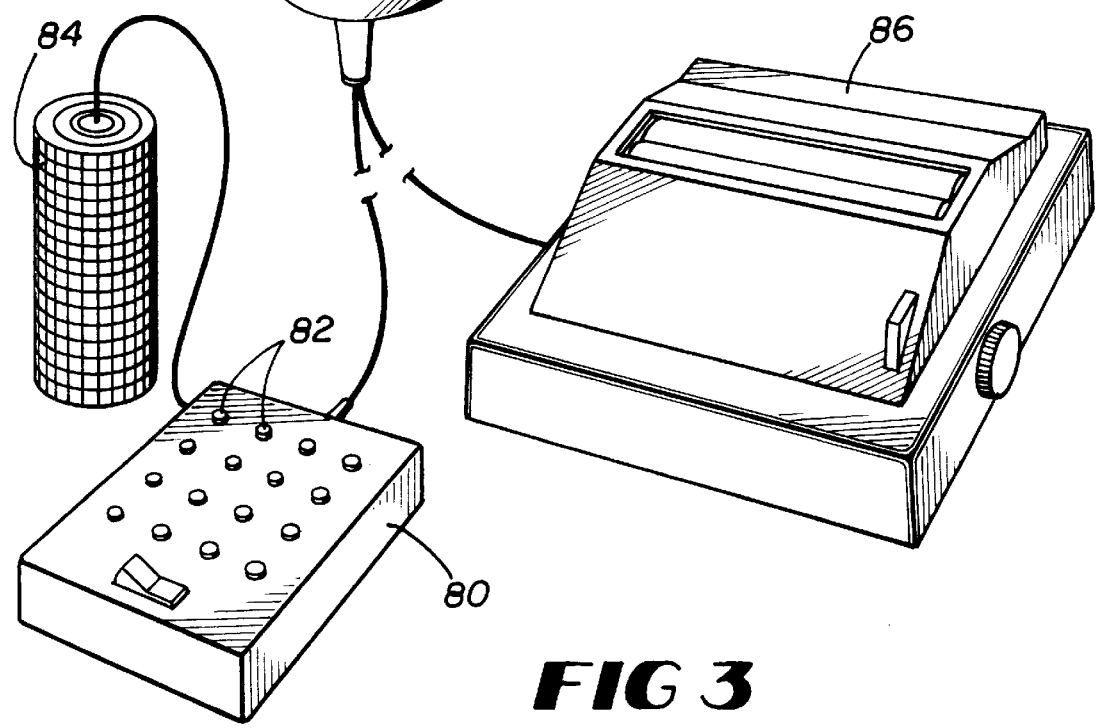

Referring to FIG. 3, in a second embodiment device 10 is connected to a control unit 80 which has a number of switches 82. Control unit 80 comprises a computer and memory. The computer can selectively control each light source 58 and does so based on a control sequence stored in the memory. Multiple control sequences can be stored in the memory, each sequence corresponding to a different test pattern. Each switch 82 allows the selection and initiation of a different test pattern. Hand switch 84 is provided so that the patient can respond when he or she detects a test signal. Control unit 80 may also be connected to a printer 86 so that a record of the test may be produced and place in the patient's medical file. The printout may include a graphical printout that mimics the distribution of light sources 58 and illustrates which light, when illuminated, did not evoke a response from the patient.

To operate device 10, the practitioner illuminates light source 58A in the center of unit 15 and instructs the patient to direct his or her eye to view source 58A. This centers the eye so that when test signals are delivered, the patient is detecting the test signal with his or her peripheral vision and not by looking towards the test signal. Thereafter, other sources 58 are sequentially illuminated in a random pattern. As each source illuminates, the patient, if he or she detects the test signal, responds verbally or by depressing handswitch 84. The results are recorded manually by the practitioner or electronically by printer 86.

When the embodiment of FIG. 2 is employed, a control sequence stored in an onboard memory of device 10 may be triggered by depressing a predetermined sequence of switches 60. Alternatively, device 10 may be operated manually by depressing switches 60, thereby illuminating corresponding sources 58.

When the embodiment of FIG. 2A is employed, external light sources 62, which correspond to light sources 58, illuminate in concert with the corresponding internal source 58. In this manner, the practitioner can observe that an internal light source 58 has been illuminated. Thereafter, if the patient does not respond the practitioner can conclude that the patient has failed to detect a test signal and record this result.

If the patient is unable to signal verbally or by pressing the handswitch 84 due to some incapacity, the practitioner can instruct the patient to look towards any test signals that he or she detects. Once the test signal has disappeared, the patient looks back to the central source 58A. Because the eyes are equally enervated, the eyes generally act in coordination. Thus, when the patient looks to the test signal, the uncovered eye will follow the movement of the eye being tested. The practitioner, by observing the movement of the uncovered eye, can thus determine whether the patient has detected the test signal.

In the case of a small child, a object such as a toy may be held before the child to distract his or her attention and bring the uncovered eye (and therefore the covered eye, as well) to a forward, centered position. As the test signal is provided, the child, if he or she detects it, will look thereto. The practitioner can then observe the uncovered eye and note movement towards the location of the test signal.

In the conventional means for assessing field of vision, the test surface onto which test signals are projected may be several feet away from the patient. Furthermore, the test signals are usually made quite dim to assure the sensitivity of the exam. As a result, someone with imperfect vision may be unable to see the test signal, not due to a lack of peripheral vision, but simply because the image is lost due to the patient's decreased visual acuity. While decreased visual acuity resulting from myopia may be accommodated with corrective lenses, such lenses may not always be available, as, for instance, in a hospital room. Furthermore, some types of visual dysfunction, such as cataracts, limit the distance viewing of a patient and cannot be corrected with lenses. In the present invention, the eye being tested is occluded from ambient light and light sources 58 are very close to the eye. As a result, the retinal image caused by light sources 58 remains blurry and the brain of a patient does not sense the light source 58 as being nearby. Thus no convergence, or "awareness of nearness," is stimulated. Instead, the patient perceives the illumination as being at an infinite distance. The actual nearness of light sources 58, however, assures that the patient will not fail to detect test signals due to a lack of visual acuity that cannot be corrected for by the testing device, such as cataracts. Because light sources 58 are in close proximity to the subject eye, testing anomalies due to lack of visual acuity are reduced or eliminated. Furthermore, the apparent infinite distance of the image allows the eye to relax, reducing eye strain and fatigue and increasing the comfort level of the patient.

The foregoing is provided for purposes of illustration, explanation, and description of embodiments of the present invention. Modifications and adaptations to these embodiments, including interchangeability among the embodiments of various features described herein, will be apparent to those of skill in the art and may be made without departing from the scope or spirit of the invention. The second set of light sources 60, for example, could be hingedly-mounted to the exterior of eyepiece 16 to permit the practitioner to confirm the illumination status of light sources 58 from varying positions relative to the patient.

I claim:

1. An apparatus for use in assessing the field of vision of a subject eye, the apparatus comprising:
   a) an eyepiece for occluding the subject eye, the eyepiece having an inner surface;
   b) a fixation light affixed to the inner surface in a position corresponding to about the center of the field of vision of the subject eye; and,
   c) a plurality of selectively illuminable light sources affixed to the inner surface and positioned so as to extend to at least the limits of peripheral vision of a normal eye.

2. The apparatus of claim 1 in which each of the selectively illuminable light sources comprises a light emitting diode (LED).

3. The apparatus of claim 2 further comprising a control unit for automatically selectively illuminating the LEDs.

4. The apparatus of claim 1 in which each of the selectively illuminable light sources comprises a liquid crystal display (LCD) pixel.

5. The apparatus of claim 4 in which each LCD pixel abuts another such pixel forming an array positioned within the occluding means and the apparatus further comprises a light source positioned between the occluding means and the array.

6. The apparatus of claim 5 further comprising a control unit for automatically selectively rendering the LCD pixels opaque.

7. The apparatus of claim 1 further comprising a response switch.

8. The apparatus of claim 7 further comprising a means for recording operations of the response switch.

9. A method for assessing the field of vision of a subject eye comprising the steps of:
   a) covering the subject eye with a testing means having a centrally located fixation light and a plurality of selectively illuminable light sources affixed to an inner surface of the testing means and positioned so as to extend at least to the limits of peripheral vision of a normal eye;
   b) illuminating the fixation light;
   c) providing test signals from a control unit to the testing means which illuminate at least one of the light sources in a location that provides an indication of the field of vision of the subject eye; and,
   d) determining the patient's response to the test signals.

10. The method of claim 9 in which the step of covering the eye to be tested is performed using a testing means comprising:
    a) an opaque housing having an internal face, an external face and a light-proof seal that substantially conforms to the patient's face about the periphery the eye;
    b) a means for securing the housing against the patient's face;
    c) a plurality of illumination sources on the internal face; and
    d) a fixation light located at the center of the internal face.

11. The method of claim 10 in which the step of providing test signals from the control unit is performed by selectively switching on or off at least one of the illumination sources.

12. The method of claim 11 in which the step of determining the patient's responses to the test signals further comprises the steps of
    a) observing an uncovered eye of the patient;
    b) determining any movement or absence of movement of the uncovered eye during the test signals.

13. A field of vision testing unit comprising:
    a) a headband;
    b) an eyepiece for occluding a subject eye connected to the headband and having an inner surface which extends at least to the limits of peripheral vision of a normal eye;
    c) a fixation light affixed to the inner surface in a position corresponding to about the center of the field of vision of the subject eye;

d) a plurality of light sources affixed to the inner surface and positioned so as to extend to at least the limits of peripheral vision of a normal eye;

e) means, connected to the eyepiece, for controlling the illumination of the fixation light and the light sources;

f) means, connected to the controlling means, for detecting a patient's response to the illumination of the light sources; and g) means, connected to the controlling means, for recording the patient's response.

14. The apparatus of claim 13 in which the controlling means comprises a computer electronically connected to the light sources, a memory electronically connected to the computer, and a plurality of switches connected to the computer.

15. The apparatus of claim 14 in which the detecting means is a handheld switch.

16. The apparatus of claim 15 in which the recording means is a printer.

* * * * *